United States Patent
Huang et al.

(10) Patent No.: US 9,063,133 B2
(45) Date of Patent: Jun. 23, 2015

(54) METHODS AND DEVICES FOR BIOMOLECULAR ARRAYS

(75) Inventors: Xiaohua Huang, La Jolla, CA (US); Kristopher D. Barbee, San Diego, CA (US)

(73) Assignee: The Regents of the University of California, La Jolla, CA (US)

(*) Notice: Subject to any disclaimer, the term of this patent is extended or adjusted under 35 U.S.C. 154(b) by 1556 days.

(21) Appl. No.: 12/525,068

(22) PCT Filed: Jan. 30, 2008

(86) PCT No.: PCT/US2008/052484
§ 371 (c)(1),
(2), (4) Date: Dec. 29, 2009

(87) PCT Pub. No.: WO2008/109207
PCT Pub. Date: Sep. 12, 2008

(65) Prior Publication Data
US 2010/0120630 A1    May 13, 2010

Related U.S. Application Data

(60) Provisional application No. 60/887,244, filed on Jan. 30, 2007.

(51) Int. Cl.
*G03F 7/00* (2006.01)
*G03F 7/16* (2006.01)
*G01N 33/543* (2006.01)
*B01J 19/00* (2006.01)
*G01N 21/64* (2006.01)

(52) U.S. Cl.
CPC .... *G01N 33/54346* (2013.01); *G01N 33/54326* (2013.01); *G03F 7/16* (2013.01); *G03F 7/00* (2013.01); *B01J 19/0046* (2013.01); *B01J 2219/00317* (2013.01); *B01J 2219/00466* (2013.01); *B01J 2219/00468* (2013.01); *B01J 2219/005* (2013.01); *B01J 2219/00576* (2013.01); *B01J 2219/00648* (2013.01); *B01J 2219/00655* (2013.01); *G01N 33/54353* (2013.01)

(58) Field of Classification Search
None
See application file for complete search history.

(56) References Cited

U.S. PATENT DOCUMENTS

| | | |
|---|---|---|
| 2003/0044855 A1 | 3/2003 | Anderson et al. |
| 2003/0077526 A1 | 4/2003 | Randall et al. |
| 2004/0029303 A1 | 2/2004 | Hart et al. |
| 2006/0273245 A1 | 12/2006 | Kim et al. |
| 2007/0020700 A1 | 1/2007 | Carpenter et al. |

OTHER PUBLICATIONS

Grego et al., Langmuir, 2005, 21:4971-4975.*
Osaka et al. (Anal. Bioanal. Chem., 2006, 384:593-600).*
Hultman et al. (Nucleic Acids Research, 1989, 13:4937-4947).*
Microposit (Microposit Product Flyer, 2006).*
(Continued)

*Primary Examiner* — Christopher M Babic
*Assistant Examiner* — Jeremy C Flinders
(74) *Attorney, Agent, or Firm* — Mintz Levin

(57) ABSTRACT

Provided herein are methods of assembling high density biomolecular arrays. The disclosed methods and devices combine a photolithographic step with the assembly of particles conjugated to biomolecules. The methods provided herein are particularly useful for the assembly of large, high density biomolecular arrays like protein arrays for chip-based assays and DNA arrays for genomic analysis.

17 Claims, 9 Drawing Sheets

(56) References Cited

OTHER PUBLICATIONS

International Search Report for Application No. PCT/US2008/052484 dated Sep. 15, 2008, 1 page.
Cui et al., "Integration of colloidal nanocrystals into lithographically patterned devices," Nano Letters 2004, 4(6):1093-1098.
Ferguson et al., "High-density fiber-optic DNA random microsphere array," Anal. Chem. Nov. 15, 2000, 72(22):5618-5624.
Li et al., "Mutiplexed analysis of polymorphisms in the HLA gene complex using bead array chips," Tissue Antigens 2004, 63:518-528.
Michael et al., "Randomly ordered addressable high-density optical sensor arrays," Anal. Chem. Apr. 1, 1998, 70(7):1242-1248.
Michel et al., "A novel approach to produce biologically relevant chemical patterns at the nanometer scale: selective molecular assembly patterning combined with colloidal lithography," Langmuir 2002, 18(22):8580-8586.

Roberts et al., "Patterned magnetic bar array for high-throughput DNA detection," IEEE Transactions on Magnetics 2004, 40(4):3006-3008.
Steemers et al., "Whole genome genotyping technologies on the BeadArray™ platform," Biotechnol. J. 2007, 2, 41-49.
Wen et al., "Two- and three-dimensional arrays of magnetic microspheres," Journal of Materials Research Apr. 1999, 14(4):1186-1189.
Xia et al., "Template-assisted self-assembly of spherical colloids into complex and controllable structures," Advanced Functional Materials 2003, 13(12):907-918.
Yellen et al., "Programmable assembly of colloidal particles using magnetic microwell templates," Langmuir 2004, 20(7):2553-2559.
Yin et al., "Template-assisted self-assembly: a practical route to complex aggregates of monodispersed colloids with well-defined sizes, shapes, and structures," J. Am. Chem. Soc., 123(36):8718-8729.

* cited by examiner

METHODS AND DEVICES FOR BIOMOLECULAR ARRAYS

CROSS-REFERENCES TO RELATED APPLICATIONS

This application claims priority under 35 U.S.C. §119(e) of U.S. Provisional Application No. 60/887,244, filed Jan. 30, 2007, the disclosure of which is hereby incorporated by reference in its entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 88654-773077_ST25.TXT, created on Mar. 26, 2013, 1,547 bytes, machine format IBM-PC, MS-Windows operating system, is hereby incorporated by reference.

STATEMENT AS TO RIGHTS TO INVENTIONS MADE UNDER FEDERALLY SPONSORED RESEARCH AND DEVELOPMENT

This invention was sponsored by the U.S. government under NIH Grant No. HG003587, and under NSF Grant No. BES0547193. As such, the U.S. government may have certain rights in the invention.

BACKGROUND OF THE INVENTION

Some of the greatest breakthroughs in biomedical research may be attributed to the development of the numerous high throughput technologies for the quantitative measurements of biomolecules. Many of these technologies are made possible by microfabrication techniques commonly used in the semiconductor industry. For example, DNA and protein arrays fabricated by robotic printing and photolithographic methods have enabled extremely large-scale surveys of biomolecules (see, Fodor, S. P. A.; Read, J. L.; Pirrung, M. C.; Stryer, L.; Lu, A. T.; Solas, D. *Science* 1991, 251, 767-773; Schena, M.; Shalon, D.; Davis, R. W.; Brown, P. O. *Science* 1995, 270, 467-470; Lockhart, D. J.; Dong, H.; Byrne, M. C.; Follettie, M. T.; Gallo, M. V.; Chee, M. S.; Mittmann, M.; Wang, C.; Kobayashi, M.; Horton, H., et al. *Nat. Biotechnol.* 1996, 14, 1675-1680; Zhu, H.; Bilgin, M.; Bangham, R.; Hall, D.; Casamayor, A.; Bertone, P.; Lan, N.; Jansen, R.; Bidlingmaier, S.; Houfek, T., et al. *Science* 2001, 293, 2101-2105). The emerging "next generation" genome sequencing technologies, many of which utilize massive parallelization and miniaturization to achieve unprecedented multiplexing, throughput and cost reductions, promise to revolutionize biomedical research and enable personalized healthcare (see, Emrich, C. A.; Tian, H.; Medintz, I. L.; Mathies, R. A. *Anal. Chem.* 2002, 74, 5076-5083; Margulies, M.; Egholm, M.; Altman, W. E.; Attiya, S.; Bader, J. S.; Bemben, L. A.; Berka, J.; Braverman, M. S.; Chen, Y. J.; Chen, Z., et al. *Nature* 2005, 437, 376-380; Shendure, J.; Porreca, G. J.; Reppas, N. B.; Lin, X.; McCutcheon, J. P.; Rosenbaum, A. M.; Wang, M. D.; Zhang, K.; Mitra, R. D.; Church, G. M. *Science* 2005, 309, 1728-1732; Bentley, D. R. *Curr. Opin. Genet. Dev.* 2006, 16, 545-552; Church, G. M. *Sci. Am.* 2006, 294, 46-54; Johnson, D. S.; Mortazavi, A.; Myers, R. M.; Wold, B. *Science* 2007, 316, 1497-1502). Some of these technology platforms utilize randomly distributed DNA-conjugated microbeads or clones on a glass slide within a reaction chamber. The random arrangements of the beads or clones however, result in low throughput and imaging efficiency, complicated image processing and high reagent costs.

One approach to dramatically improve these devices involves the use of microfabricated arrays to eliminate overlap and to minimize the area between the beads or clones. Such arrays may be generated by depositing samples onto glass slides using robotic contact printing, micro-contact printing or dip pen lithography (see, Schena, M.; Shalon, D.; Davis, R. W.; Brown, P. O. *Science* 1995, 270, 467-470; Thibault, C.; Berm, V. L.; Casimirius, S.; Trévisiol, E.; Francois, J.; Vieu, C. *J. Nanobiotech.* 2005, 3, 1-12; Pla-Roca, M.; Fernandez, J. G.; Mills, C. A.; Martinez, E.; Samitier, J. *Langmuir* 2007, 23, 8614-8618; Tan, H.; Huang, S.; Yang, K. L. *Langmuir* 2007, 23, 8607-8613; Nam, J.-M.; Han, S. W.; Lee, K.-B.; Liu, X.; Rathner, M. A.; Mirkin, C. A. *Angew*). These arrays may also be generated by assembling beads onto microfabricated arrays of wells on glass or silicon substrates, or in etched wells on the face of a fiber-optic bundle (see, Xia, Y.; Yin, Y.; Lu, Y.; McLellan, J. *Adv. Funct. Mater.* 2003, 13, 907-918; Michel, R.; Reviakine, I.; Sutherland, D.; Fokas, C.; Csucs, G.; Danuser, G.; Spencer, N. D.; Textor, M. *Langmuir* 2002, 18, 8580-8586; Cui, Y.; Bjork, M. T.; Liddle, J. A.; Sonnichsen, C.; Boussert, B.; Alivisatos, A. P. *Nano Lett.* 2004, 4, 1093-1098; Steemers, F. J.; Gunderson, K. L. *Biotechnol. J.* 2007, 2, 41-49; Michael, K. L.; Taylor, L. C.; Schultz, S. L.; Walt, D. R. *Anal. Chem.* 1998, 70, 1242-1248; Ferguson, J. A.; Steemers, F. J.; Walt, D. R. *Anal. Chem.* 2000, 72, 5618-5624) Since bead assembly may not occur in an efficient and reliable manner if the process depends solely upon gravitational forces and Brownian motion, this process is typically achieved via solvent evaporation or de-wetting (see, Cui, Y.; Bjork, M. T.; Liddle, J. A.; Sonnichsen, C.; Boussert, B.; Alivisatos, A. P. Nano Lett. 2004, 4, 1093-1098; Steemers, F. J.; Gunderson, K. L. *Biotechnol. J.* 2007, 2, 41-49; Michael, K. L.; Taylor, L. C.; Schultz, S. L.; Walt, D. R. *Anal. Chem.* 1998, 70, 1242-1248; Ferguson, J. A.; Steemers, F. J.; Walt, D. R. *Anal. Chem.* 2000, 72, 5618-5624; Yin, Y.; Lu, Y.; Gates, B.; Xia, Y. *J. Am. Chem. Soc.* 2001, 123, 8718-8729). These approaches however, are not suitable when rapid assembly is required or sample drying is undesirable.

Other groups have employed electric and magnetic assembly methods to overcome these issues, but these active approaches require multi-step fabrication processes and complex field generation schemes (see, Li, A. X.; Seul, M.; Cicciarelli, J.; Yang, J. C.; Iwaki, Y. *Tissue Antigens* 2004, 63, 518-528; Wen, W.; Wang, N.; Zheng, D. W.; Chen, C.; Tu, K. N. *J. Mater. Res.* 1999, 14; Roberts, L. A.; Crawford, A. M.; Zappe, S.; Jain, M.; White, R. L. *IEEE Trans. Magnet.* 2004, 40, 3006-3008; Yellen, B. B.; Friedman, G. *Langmuir* 2004, 20, 2553-2559).

For many genomic and proteomic applications however, the array fabrication and assembly processes also need to be scalable and inexpensive, and the format of the arrays must also be compatible with high-throughput imaging and microfluidic devices. Thus, there remains a need in the art for improved high throughput technologies for biomolecules.

BRIEF SUMMARY OF THE INVENTION

Disclosed herein are methods and devices for rapidly assembling high density biomolecular arrays, including protein arrays for chip-based assays, and DNA arrays for genomic analysis. The disclosed methods and devices combine a photolithographic step with the assembly of nanoparticles or magnetic microbeads conjugated to a biomolecule, to create large, high density biomolecular arrays.

In one aspect the disclosure provides methods for rapidly assembling a high density biomolecular array, by: a) patterning an array of wells into photoresist on a surface by photolithography; b) assembling a suspension of particles into the array of wells; c) immobilizing the particles to the surface via affinity binding; and d) removing the unbound suspension of particles and photoresist from the surface to provide the high density biomolecular array.

In another aspect the disclosure provides methods for rapidly assembling a high density biomolecular array, by: a) patterning an array of wells into photoresist on a surface by photolithography; b) assembling a suspension of particles into the array of wells; c) immobilizing the particles to the surface via affinity binding; and d) removing the unbound suspension of particles and photoresist from the surface to provide the high density biomolecular array, wherein the suspension of particles conjugated to a biomolecule is a suspension of superparamagnetic microbeads conjugated to a biomolecule, wherein the superparamagnetic microbeads are assembled into the array of wells using a magnet.

In another aspect the disclosure provides methods for rapidly assembling a high density biomolecular array, by: a) patterning an array of wells into photoresist on a surface by photolithography; b) assembling a suspension of particles into the array of wells; c) immobilizing the particles to the surface via affinity binding; and d) removing the unbound suspension of particles and photoresist from the surface to provide the high density biomolecular array, wherein the suspension of particles conjugated to a biomolecule is a suspension nanoparticles conjugated to a biomolecule.

In another aspect the disclosure provides methods for rapidly assembling a high density biomolecular array, by: a) patterning an array of wells into photoresist on a surface by photolithography; b) assembling a suspension of particles into the array of wells; c) immobilizing the particles to the surface via affinity binding; and d) removing the unbound suspension of particles and photoresist from the surface to provide the high density biomolecular array, wherein the suspension of particles conjugated to a biomolecule is a suspension nanoparticles conjugated to a biomolecule, and wherein the surface is derivatized with a biotin-derivatized and/or amine-derivatized cross-linked polyacrylamide polymer, wherein the cross-linked polyacrylamide polymer is coated with photoresist.

DETAILED DESCRIPTION OF THE INVENTION

Figure 1:
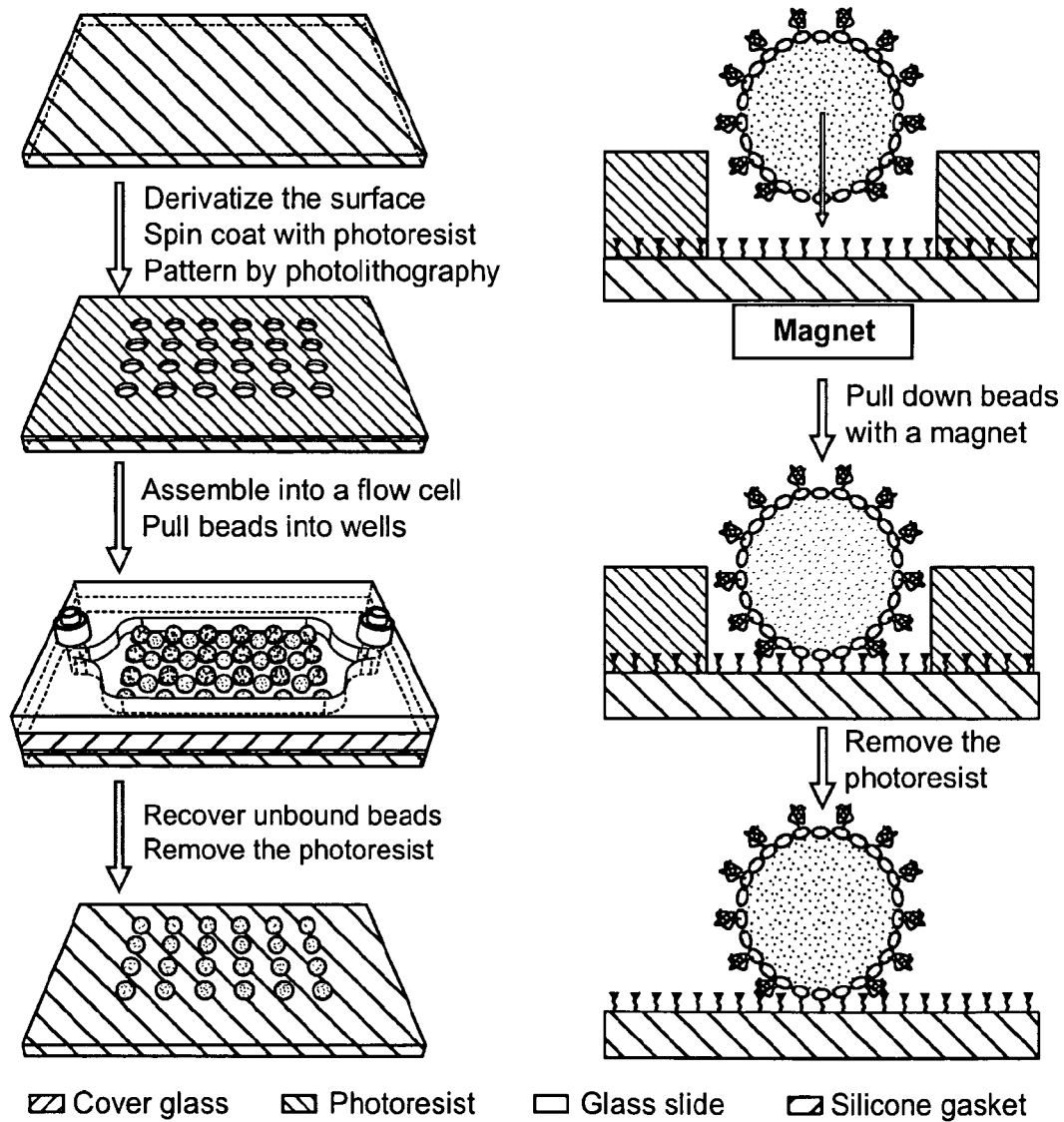
FIG. 1 illustrates the rapid assembly of high density biomolecular arrays, such as protein and/or DNA arrays, and the steps involved in the fabrication and assembly process.

Disclosed herein are methods and devices for rapidly assembling high density biomolecular arrays, including protein arrays for chip-based assays, and DNA arrays for genomic analysis. The disclosed methods and devices combine a photolithographic step with the assembly of nanoparticles or magnetic microbeads conjugated to a biomolecule, to create large, high density biomolecular arrays.

The disclosed methods provide wafer-scale arrays of microwells in a layer of photoresist prepared by photolithograph techniques on a chemically functionalized glass surface. The arrays may be enclosed within a microfluidic device and a suspension of nanoparticles or superparamagnetic microbeads conjugated to a biomolecule is introduced into the chamber. The nanoparticles may self-assemble or be directed into the wells through an electrical field. Alternatively, a magnet may be used to direct the assembly of the beads into the wells. In the disclosed arrays, each well contains a single bead. The nanoparticles and supermagnetic beads may be immobilized onto a glass surface or cross-linked onto a polyacrylamide surface via affinity binding and any excess particles or supermagnetic beads may be recycled or washed away. Non-specifically bound particles and supermagnetic beads may be removed by removing the photoresist using an alcoholic solvent. The result is a high density array of nanoparticles or supermagnetic beads conjugated to a biomolecule, with virtually no background. These methods may be used to produce protein arrays for chip-based assays and DNA arrays for genotyping or genome sequencing.

Photoresist is a light-sensitive material used in several industrial process, such as photolithography and photoengraving, to form a patterned coating on a surface. Photoresists may be classified into two groups: positive resists and negative resists. A positive resist is a type of photoresist in which the portion of the photoresist that is exposed to light becomes soluble to the photoresist developer and the portion of the photoresist that is unexposed remains insoluble to the photoresist developer. A negative resist is a type of photoresist in which the portion of the photoresist that is exposed to light becomes relatively insoluble to the photoresist developer. The unexposed portion of the photoresist is dissolved by the photoresist developer.

Photoresists are most commonly used at wavelengths in the ultraviolet spectrum or shorter (<400 nm). For example, diazonaphthoquinone (DNQ) absorbs strongly from approximately 300 nm to 450 nm. The absorbed energy can drive further reactions and ultimately dissipates as heat. This is associated with the outgassing and contamination from the Photoresist. Photoresists may also be exposed by electron beams, producing the same results as exposure by light. One very common positive photoresist used with the I, G and H-lines from a mercury-vapor lamp is based on a mixture of Diazonaphthoquinone (DNQ) and Novolac resin (a phenol formaldehyde resin). DNQ inhibits the dissolution of the novolac resin, however, upon exposure to light, the dissolution rate increases even beyond that of pure novolac. The mechanism by which unexposed DNQ inhibits novolac dissolution is not well understood, but is believed to be related to hydrogen bonding (or more exactly diazocoupling in the unexposed region). DNQ-novolac resists are developed by dissolution in a basic solution (usually 0.26N tetra-methyl ammonium hydroxide in water). One very common negative photoresist is based on an epoxy-based polymer. The common product name is SU-8 photoresist.

Deep Ultraviolet (DUV) resist are typically polyhydroxystyrene-based polymers with a photoacid generator providing the solubility change. However, this material does not experience the diazocoupling. The combined benzene-chromophore and DNQ-novolac absorption mechanisms lead to stronger absorption by DNQ-novolac photoresists in the DUV, requiring a much larger amount of light for sufficient exposure. The strong DUV absorption results in diminished photoresist sensitivity.

Photoresists used in production for DUV and shorter wavelengths require the use of chemical amplification to increase the sensitivity to the exposure energy. This is done in order to combat the larger absorption at shorter wavelengths. Chemical amplification is also often used in electron-beam exposures to increase the sensitivity to the exposure dose. In the process, acids released by the exposure radiation diffuse during the post-exposure bake step. These acids render surrounding polymer soluble in developer. A single acid molecule can catalyze many such deprotection reactions; hence, fewer photons or electrons are needed. Acid diffusion is important not only to increase photoresist sensitivity and throughput, but also to limit line edge roughness due to shot noise statistics. However, the acid diffusion length is itself a potential resolution limiter. In addition, too much diffusion reduces chemical contrast, leading again to more roughness.

Thus, in one aspect the disclosure provides methods for rapidly assembling a high density biomolecular array by: a) patterning an array of wells into photoresist on a surface by photolithography; b) assembling a suspension of particles into the array of wells; c) immobilizing the particles to the surface via affinity binding; and d) removing the unbound suspension of particles and photoresist from the surface to provide the high density biomolecular array.

In another aspect the disclosure provides methods for rapidly assembling a high density biomolecular array by a) chemically derivatizing a surface; b) coating the surface with photoresist; c) patterning an array of wells into the photoresist by photolithography; d) exposing the array of wells to a suspension of particles conjugated to a biomolecule; e) assembling a suspension of particles into the array of wells; f) immobilizing the particles to the surface via affinity binding; g) removing the unbound suspension of particles; and h) removing the photoresist from the surface to provide the high density biomolecular array.

In another aspect the disclosure provides methods for rapidly assembling a high density biomolecular array, wherein the suspension of particles conjugated to a biomolecule is a suspension of superparamagnetic microbeads conjugated to a biomolecule, wherein the superparamagnetic microbeads are assembled into the array of wells using a magnet.

In another aspect the disclosure provides methods for rapidly assembling a high density biomolecular array, wherein the surface is a glass surface.

In another aspect the disclosure provides methods for rapidly assembling a high density biomolecular array, wherein the glass surface is derivatized with silane and biotin, and/or avidin and/or streptavidin.

In another aspect the disclosure provides methods for rapidly assembling a high density biomolecular array, wherein the glass surface is spin-coated with photoresist.

In another aspect the disclosure provides methods for rapidly assembling a high density biomolecular array, wherein the photoresist is sold under the trademark MICROPOSIT™ S1805™.

In another aspect the disclosure provides methods for rapidly assembling a high density biomolecular array, wherein the array of wells are patterned by photolithography using a 0.2 second exposure to 365 nM light (~475 mW/cm$^2$) through a chrome-on-quartz photomask using a wafer stepper system (GCA Autostep 200) equipped with an Olympus 2145 lens (5× reduction/0.45 NA).

In another aspect the disclosure provides methods for rapidly assembling a high density biomolecular array, wherein the size of the array of wells varies with the exposure and chemical etching parameters of the photolithography technique.

In another aspect the disclosure provides methods for rapidly assembling a high density biomolecular array, wherein the array of wells has a density of about 100 million wells per square centimeter.

In another aspect the disclosure provides methods for rapidly assembling a high density biomolecular array, wherein the array of wells has a parabolic geometry wherein the top of a well is about 600 nm in diameter and the bottom of a well is about 250 nm in diameter.

In another aspect the disclosure provides methods for rapidly assembling a high density biomolecular array, wherein the superparamagnetic microbeads are coated with biotin, and/or avidin and/or streptavidin.

In another aspect the disclosure provides methods for rapidly assembling a high density biomolecular array, wherein the superparamagnetic microbeads are suspended in a buffer.

In another aspect the disclosure provides methods for rapidly assembling a high density biomolecular array, wherein the assembly of the superparamagnetic microbeads into the array of wells occurs in a flow cell.

In another aspect the disclosure provides methods for rapidly assembling a high density biomolecular array, wherein the superparamagnetic microbeads are assembled into the array of wells using a neodymium iron boron magnet.

In another aspect the disclosure provides methods for rapidly assembling a high density biomolecular array, wherein each well contains a single superparamagnetic microbead.

In another aspect the disclosure provides methods for rapidly assembling a high density biomolecular array, wherein the superparamagnetic microbeads are immobilized in the array of wells via biotin-avidin and/or biotin-streptavidin affinity binding.

In another aspect the disclosure provides methods for rapidly assembling a high density biomolecular array, wherein the high density biomolecular array is a high density protein array, or a high density DNA array of biomolecules.

In another aspect the disclosure provides a high density biomolecular array prepared by: a) chemically derivatizing a surface; b) coating the surface with photoresist; c) patterning an array of wells into the photoresist by photolithography; d) exposing the array of wells to a suspension of particles conjugated to a biomolecule; e) assembling a suspension of particles into the array of wells; f) immobilizing the particles to the surface via affinity binding; g) removing the unbound suspension of particles; and h) removing the photoresist from the glass surface to provide the high density biomolecular array.

In another aspect the disclosure provides a high density biomolecular array prepared by: a) chemically derivatizing a surface; b) coating the surface with photoresist; c) patterning an array of wells into the photoresist by photolithography; d) exposing the array of wells to a suspension of particles conjugated to a biomolecule; e) assembling a suspension of particles into the array of wells; f) immobilizing the particles to the surface via affinity binding; g) removing the unbound suspension of particles; and h) removing the photoresist from the glass surface to provide the high density biomolecular array, wherein the suspension of particles conjugated to a biomolecule is a suspension of superparamagnetic microbeads conjugated to a biomolecule, and wherein the suspension of superparamagnetic microbeads are assembled into the array of wells using a magnet.

In another aspect the disclosure provides methods for rapidly assembling a high density biomolecular array by: a) chemically derivatizing a surface; b) coating the surface with photoresist; c) patterning an array of wells into the photoresist by photolithography; d) exposing the array of wells to a suspension of particles conjugated to a biomolecule; e) assembling a suspension of particles into the array of wells; f) immobilizing the particles to the surface via affinity binding; g) removing the unbound suspension of particles; and h) removing the photoresist from the surface to provide the high density biomolecular array, wherein the suspension of particles conjugated to a biomolecule is a suspension nanoparticles conjugated to a biomolecule.

In another aspect the disclosure provides methods for rapidly assembling a high density biomolecular array, wherein the surface is a glass surface.

In another aspect the disclosure provides methods for rapidly assembling a high density biomolecular array, wherein the glass surface is derivatized with silane and biotin, and/or avidin and/or streptavidin.

In another aspect the disclosure provides methods for rapidly assembling a high density biomolecular array, wherein the glass surface is spin-coated with photoresist.

In another aspect the disclosure provides methods for rapidly assembling a high density biomolecular array, wherein the photoresist is sold under the trademark MICROPOSIT™ S1805™.

In another aspect the disclosure provides methods for rapidly assembling a high density biomolecular array, wherein the array of wells are patterned by photolithography using a 0.2 second exposure to 365 nM light (~475 mW/cm$^2$) through a chrome-on-quartz photomask using a wafer stepper system (GCA Autostep 200) equipped with an Olympus 2145 lens (5× reduction/0.45 NA).

In another aspect the disclosure provides methods for rapidly assembling a high density biomolecular array, wherein the size of the array of wells varies with the exposure and chemical etching parameters of the photolithography technique.

In another aspect the disclosure provides methods for rapidly assembling a high density biomolecular array, wherein the array of wells has a density of about 100 million wells per square centimeter.

In another aspect the disclosure provides methods for rapidly assembling a high density biomolecular array, wherein the array of wells has a parabolic geometry wherein the top of a well is about 600 nm in diameter and the bottom of a well is about 250 nm in diameter.

In another aspect the disclosure provides methods for rapidly assembling a high density biomolecular array, wherein the nanoparticles are coated with biotin, and/or avidin and/or streptavidin.

In another aspect the disclosure provides methods for rapidly assembling a high density biomolecular array, wherein the nanoparticles are suspended in a buffer.

In another aspect the disclosure provides methods for rapidly assembling a high density biomolecular array, wherein the assembly of the nanoparticles into the array of wells occurs in a flow cell.

In another aspect the disclosure provides methods for rapidly assembling a high density biomolecular array, wherein the nanoparticles self assemble into the array of wells.

In another aspect the disclosure provides methods for rapidly assembling a high density biomolecular array, wherein each well contains a single nanoparticle.

In another aspect the disclosure provides methods for rapidly assembling a high density biomolecular array, wherein the nanoparticles are immobilized in the array of wells via biotin-avidin and/or biotin-streptavidin affinity binding.

In another aspect the disclosure provides methods for rapidly assembling a high density biomolecular array, wherein the high density nanoarray of biomolecules is a high density nanoarray of protein, or a high density nanoarray of DNA of biomolecules.

In another aspect the disclosure provides a high density nanoarray of biomolecules prepared by: a) chemically derivatizing a surface; b) coating the surface with photoresist; c) patterning an array of wells into the photoresist by photolithography; d) exposing the array of wells to a suspension of particles conjugated to a biomolecule; e) assembling a suspension of particles into the array of wells; f) immobilizing the particles to the surface via affinity binding; g) removing the unbound suspension of particles; and h) removing the photoresist from the surface to provide the high density biomolecular array, wherein the suspension of particles conjugated to a biomolecule is a suspension nanoparticles conjugated to a biomolecule.

In another aspect the disclosure provides methods for rapidly assembling a high density biomolecular array by: a) chemically derivatizing a surface; b) coating the surface with photoresist; c) patterning an array of wells into the photoresist by photolithography; d) exposing the array of wells to a suspension of particles conjugated to a biomolecule; e) assembling a suspension of particles into the array of wells; f) immobilizing the particles to the surface via affinity binding; g) removing the unbound suspension of particles; and h) removing the photoresist from the surface to provide the high density biomolecular array, wherein the suspension of particles conjugated to a biomolecule is a suspension nanoparticles conjugated to a biomolecule, and wherein the surface is derivatized with a biotin-derivatized and/or amine-derivatized cross-linked polyacrylamide polymer, wherein the cross-linked polyacrylamide polymer is coated with photoresist.

In another aspect the disclosure provides methods for rapidly assembling a high density biomolecular array, wherein the surface is a glass surface.

In another aspect the disclosure provides methods for rapidly assembling a high density biomolecular array, wherein the glass surface is coated with a biotin-derivatized cross-linked polyacrylamide polymer.

In another aspect the disclosure provides methods for rapidly assembling a high density biomolecular array, wherein the biotin-derivatized cross-linked polyacrylamide polymer is spin-coated with photoresist.

In another aspect the disclosure provides methods for rapidly assembling a high density biomolecular array, wherein the photoresist is sold under the trademark MICROPOSIT™ S1805™.

In another aspect the disclosure provides methods for rapidly assembling a high density biomolecular array, wherein the array of wells are patterned by photolithography using a 0.2 second exposure to 365 nM light (~475 mW/cm$^2$) through a chrome-on-quartz photomask using a wafer stepper system (GCA Autostep 200) equipped with an Olympus 2145 lens (5× reduction/0.45 NA).

In another aspect the disclosure provides methods for rapidly assembling a high density biomolecular array, wherein the size of the array of wells varies with the exposure and chemical etching parameters of the photolithography technique.

In another aspect the disclosure provides methods for rapidly assembling a high density biomolecular array, wherein the array of wells has a density of about 100 million wells per square centimeter.

In another aspect the disclosure provides methods for rapidly assembling a high density biomolecular array, wherein the array of wells has a parabolic geometry wherein the top of a well is about 600 nm in diameter and the bottom of a well is about 250 nm in diameter.

In another aspect the disclosure provides methods for rapidly assembling a high density biomolecular array, wherein the nanoparticles are coated with biotin, and/or avidin and/or streptavidin.

In another aspect the disclosure provides methods for rapidly assembling a high density biomolecular array, wherein the nanoparticles are suspended in a buffer.

In another aspect the disclosure provides methods for rapidly assembling a high density biomolecular array, wherein the assembly of the nanoparticles into the array of wells occurs in a flow cell.

In another aspect the disclosure provides methods for rapidly assembling a high density biomolecular array, wherein the nanoparticles are assembled into the array of wells by an electric field.

In another aspect the disclosure provides methods for rapidly assembling a high density biomolecular array, wherein each well contains a single nanoparticle.

In another aspect the disclosure provides methods for rapidly assembling a high density biomolecular array, wherein the nanoparticles are immobilized in the array of wells via biotin-avidin and/or biotin-streptavidin affinity binding.

In another aspect the disclosure provides methods for rapidly assembling a high density biomolecular array, wherein the high density nanoarray of biomolecules is a high density nanoarray of protein, or a high density nanoarray of DNA of biomolecules.

In another aspect the disclosure provides a high density nanoarray of biomolecules prepared by: a) chemically derivatizing a surface; b) coating the surface with photoresist; c) patterning an array of wells into the photoresist by photolithography; d) exposing the array of wells to a suspension of particles conjugated to a biomolecule; e) assembling a suspension of particles into the array of wells; f) immobilizing the particles to the surface via affinity binding; g) removing the unbound suspension of particles; and h) removing the photoresist from the surface to provide the high density biomolecular array, wherein the suspension of particles conjugated to a biomolecule is a suspension nanoparticles conjugated to a biomolecule, and wherein the surface is derivatized with a biotin-derivatized and/or amine-derivatized cross-linked polyacrylamide polymer, wherein the cross-linked polyacrylamide polymer is coated with photoresist.

In another aspect the disclosure provides an automated system for rapidly assembling a high density biomolecular array, comprising a microfluidic flowcell containing an array of wells on a chemically derivatized surface coated with photoresist; a suspension of superparamagnetic microbeads conjugated to a biomolecule, and a magnet, wherein the superparamagnetic microbeads are assembled into the array of wells using the magnet.

FIG. 1 illustrates the rapid assembly of high density biomolecular arrays, such as protein and/or DNA arrays, and the steps involved in the fabrication and assembly process. The left panel shows the basic procedure used in making these arrays, whereas the right panel illustrates the surface chemistry used to attach the magnetic beads to the array and the DNA to the beads. The final microbead array is shown without the flow cell for illustrative purposes only. The drawing is not to scale.

As shown in FIG. 1, the disclosed methods for fabricating high density biomolecular arrays begins with derivatizing a surface such as a glass surface. For example, silanization and biotinylation of a glass cover slip. Photolithography is then used to generate high density arrays of micrometer to sub-micrometer scale wells in a thin layer of photoresist that has been spin coated on the glass surface. The patterned glass cover slip may be enclosed within a flow cell and a suspension of avidin- or streptavidin-coated superparamagnetic microbeads conjugated to a biomolecule, for example a protein or DNA molecule, is introduced into the device. A permanent magnet is briefly dragged along the back side of the cover glass to direct the rapid assembly of the microbeads into the wells. The beads are immobilized in the wells via biotin-avidin and/or biotin-streptavidin affinity binding with only one bead fixed within each well due to physical constraints. Excess beads are washed away and non-specifically bound beads are removed by dissolving the photoresist with an alcoholic solvent, for example, methanol or ethanol. The result is a high density array of single beads with virtually no background.

Using these procedures (see, Examples), wafer-scale high density arrays of microbeads on glass cover slips are fabricated. Specifically, large arrays of wells with micrometer to sub-micrometer dimensions may be fabricated on derivatized cover glass and millions of protein and/or DNA-conjugated superparamagnetic beads may be assembled within these wells in seconds by active manipulation with a magnetic field gradient. The light micrographs, i.e., the AFM and SEM images, of the disclosed arrays are shown in FIGS. 2 and 3.

Figure 2:
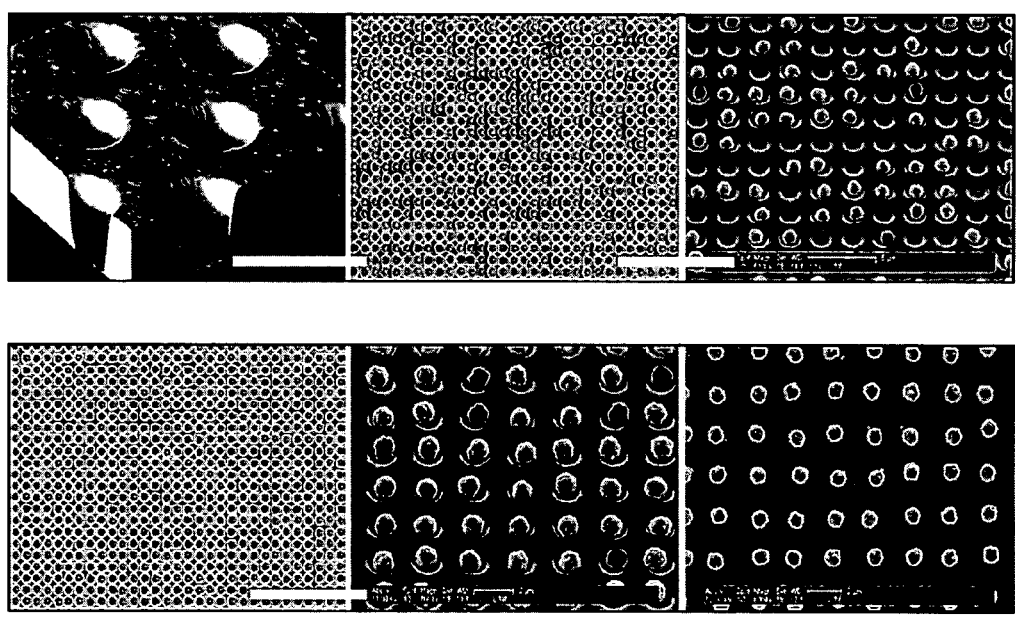
FIG. 2 illustrates the high density array of wells and microbeads.

FIG. 2 illustrates the high density array of wells and microbeads. In this figure, (A) illustrates the AFM image of a small section of an array of wells in photoresist on a glass cover slip; (B) illustrates the light micrograph image; and (C) illustrates the SEM image of a small section of an array of wells partially filled with streptavidin-conjugated superparamagnetic microbeads wherein about half of the wells were left unfilled for illustrative purposes. (D) illustrates the light micrograph image; (E) illustrates the SEM image of a highly ordered array of microbeads in wells in the photoresist; and (F) illustrates the SEM image of an array of microbeads after removal of the photoresist. This array was fabricated on a 50×75× 0.170 mm$^3$ glass cover slip and contained over 300 million wells. The wells are approximately 500 nm deep, 1.2 μm in diameter and have a center-to-center spacing of 2.4 μm. The beads have an average diameter of 1.05 μm with a maximum coefficient of variation of 3% according to the manufacturer's specifications. The scale bar in the xy-plane in (A) is 2 μm.

The vertical dimension in this AFM image is not to scale. The scale bars in (B) and (D) are 24 μm.

Figure 3:
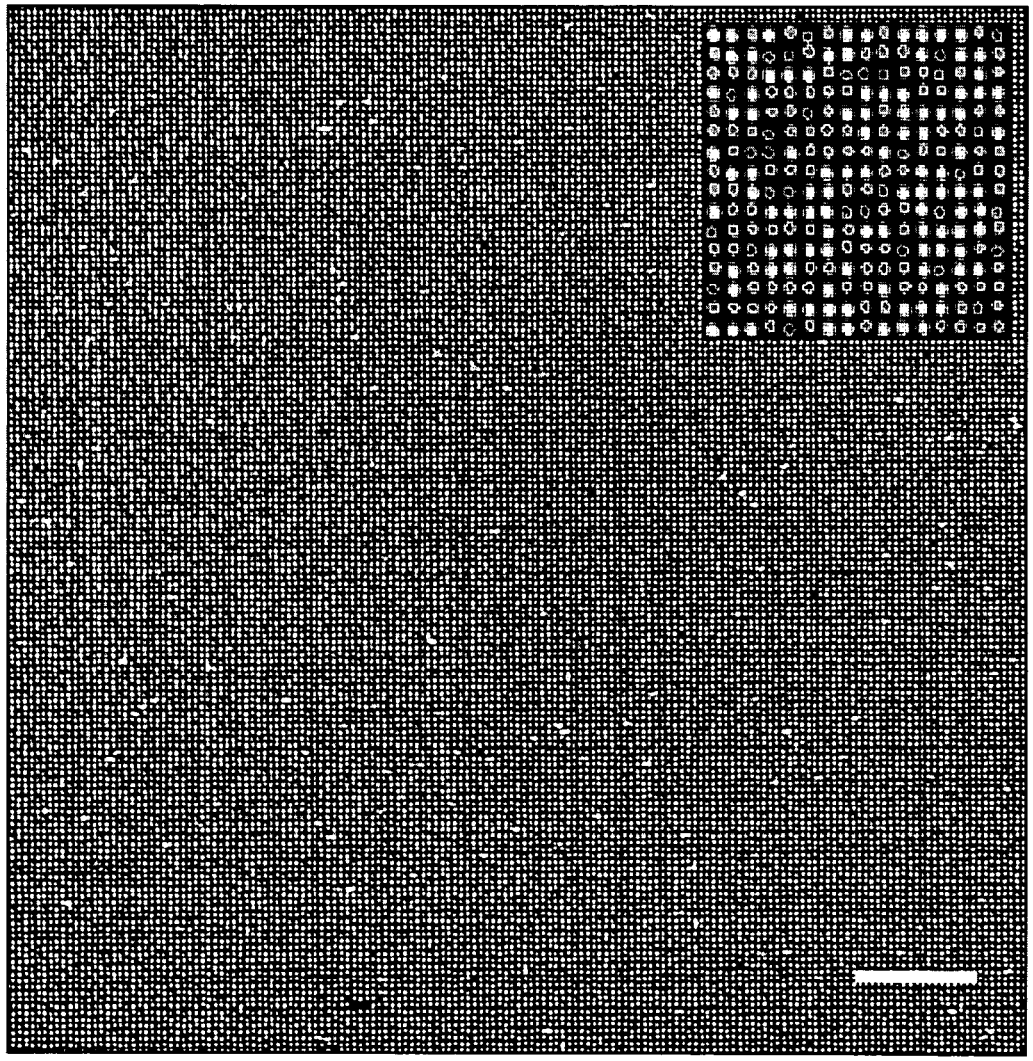
FIG. 3 illustrates an assembly of a highly ordered DNA array.

FIG. 3 illustrates an assembly of a highly ordered DNA array. A false-color composite fluorescence image of a small portion of a microbead array acquired with a 1-megapixel EMCCD camera with 8×8 μm² pixels through a 20× objective. A magnetic field gradient was applied to facilitate the rapid assembly of a mixture of three populations of 1 μm superparamagnetic beads conjugated to fluorescent dye-labeled (Fluorescein-Cyan, Cy3-Yellow, and Cy5-Red) DNA molecules. The full image from the camera is shown. The inset is an enlarged image of a region of the array. It is pixelated because only 6×6 pixels are used for each feature. The assembly process is conducted within a fluidic chamber and results in greater than 99.9% filling, with only one bead in each well, in seconds. The rare occurrence of misplaced beads (<0.5%) is very likely due to the presence of aggregates in the stock bead suspension. The center-to-center spacing of these beads is 2.4 μm. The scale bar in the main image is 48 μm. The scale bar in the inset is 12 μm.

Without the use of a magnetic field gradient, the wells filled very slowly and many of them remained empty despite prolonged incubation periods. This process is even more problematic when using beads with densities near that of water. Dewetting may be used to ensure a higher filling efficiency but it may take hours to days to fill the wells on a large array using this approach because of the slow rate at which the liquid front must move (~1 mm/h to ~1 μm/s). The application of a magnetic field gradient overcomes this limitation by rapidly concentrating the superparamagnetic beads near the surface of the array and pulling them into the wells. Since the exposure to the magnetic field gradient is very brief and does not require micromagnets or solenoids, the formation of bead aggregates is transient and does not lead to any defects on the array. Real time monitoring of the filling process may be used to determine when the assembly process is complete. Unbound beads may be drawn away from the surface using the magnet, which allows us to observe the surface of the array without having to remove the excess beads from the chamber.

The majority of the wells on a large array may be filled within seconds by quickly dragging an edge of a strong permanent magnet across the bottom of the glass substrate. By repeatedly agitating the suspension and concentrating the beads at the surface using the magnet, greater than 99.9% of the wells may be filled in less than one minute. Achieving this level of filling in such a short period of time requires a suspension containing at least $1.5 \times 10^6$ beads/μL for an array of wells with a pitch of 2.4 μm in a chamber with a height of 250 μm. This concentration corresponds to approximately twice as many beads as there are wells on this array. The use of lower concentrations will generally result in an increase in the number of empty wells and the amount of time required to fill the wells. However, even if the bead to well ratio is reduced to one, over 95% of the wells may be filled in less than 5 minutes.

The disclosed methods also provide an easy way to recycle excess beads and the process may be fully automated. These features may be much more difficult to implement when employing a dewetting or solvent evaporation approach (Yin, Y.; Lu, Y.; Xia, Y. *J. Am. Chem. Soc.* 2001, 123, 771-772; Gunderson, K. L.; Kruglyak, S.; Graige, M. S.; Garcia, F.; Kermani, B. G.; Zhao, C.; Che, D.; Dickinson, T.; Wickham, E.; Bierle, J., et al. *Genome Res.* 2004, 14, 870-877). In addition, the immobilization of the beads onto the surface via biotin-avidin and/or biotin-streptavidin binding allows for conducting various reactions and assays within the flow cell and perform rigorous washing steps without worrying about beads falling out of their wells.

Another advantage of using a capture mechanism rather than relying only on van der Waals interactions to hold the beads in place is that it permits the removal of the photoresist after the assembly process is complete. This helps to remove any remaining unbound beads from the surface, reduces background fluorescent generated by the photoresist and prevents the non-specific binding of other molecules that will eventually be introduced into the flow cell as part of an assay or reaction. These important benefits may still be realized even if biotin-avidin and/or biotin-streptavidin chemistry is not suitable for a particular application. In such cases the disclosed process may be modified to incorporate other affinity binding modalities or covalent bonds if the surfaces of the beads and the glass substrate are appropriately functionalized, e.g. with alkyne groups on the beads and azide groups on the glass surface using the "click chemistry" strategy (see, Wu, P.; Feldman, A. K.; Nugent, A. K.; Hawker, C. J.; Scheel, A.; Voit, B.; Pyun, J.; Frechet, J. M.; Sharpless, K. B.; Fokin, V. V. *Angew. Chem. Int. Ed. Engl.* 2004, 43, 3928-3932; Rozkiewicz, D. I.; Gierlich, J.; Burley, G. A.; Gutsmiedl, K.; Carell, T.; Ravoo, B. J.; Reinhoudt, D. N. *Chembiochem.* 2007, DOI: 10.1002/cbic.200700402).

Compared to fiber-optic bead arrays, the disclosed methods offer more flexibility in terms of the substrates that may be used and the format and size of the arrays that may be produced. For example, silicon wafers or various plastics may be used instead of glass. In addition, the photolithographic process allows the easy modification of every geometric parameter relevant to the arrays and provides the ability to align the beads to virtually any CCD sensor using a standard microscope rather than a fiber optic couple. Many of the beads in the figures are not perfectly aligned with one another because the wells are slightly larger than the beads. The use of oversized wells results in shorter bead assembly times and ensures that beads with larger than average diameters may still be captured. However, the well size may be reduced to match the bead size if an array with more precise alignment is required. Well diameters may be adjusted to some degree by varying the exposure time, which gives this process greater flexibility in terms of the size of beads than may be used with a given photomask.

The disclosed methods not only provide fabrication processes which result in enhanced packing efficiency, but the usage of these ordered arrays may also improve imaging efficiency and dramatically simplify image processing. The imaging efficiency, in terms of the number of pixels needed to image each feature, is given by $(M*d/p)^2$, where M is the magnification, d is the periodic distance between two adjacent features and p is the pixel size. A feature refers to a bead and its surrounding space and the equation assumes that the array is properly aligned to the CCD sensor. To achieve optimal alignment, precise adjustments to both the array and CCD are usually required. Translational positioning of the array may be performed using a motorized stage while angle adjustments may be made by rotating the camera.

Figure 4:
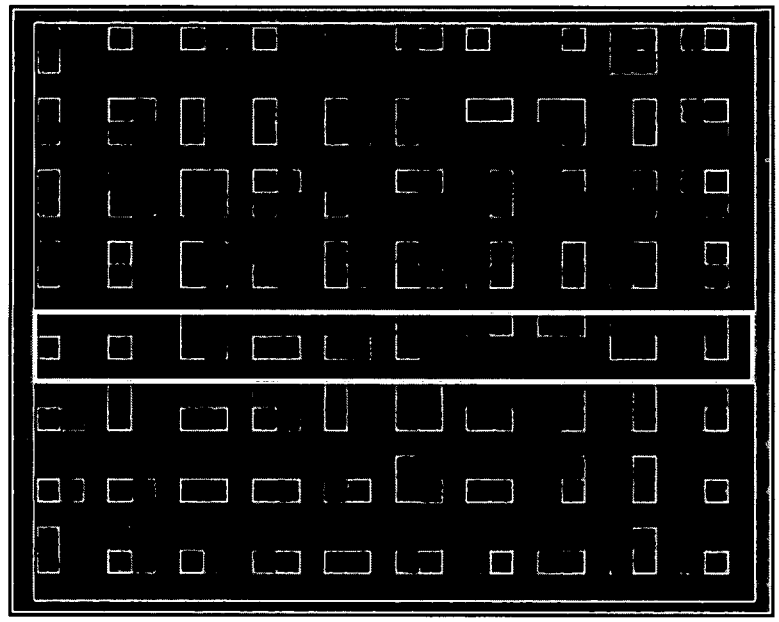
FIG. 4 illustrates the improvement of imaging efficiency and processing.
Figure 4:
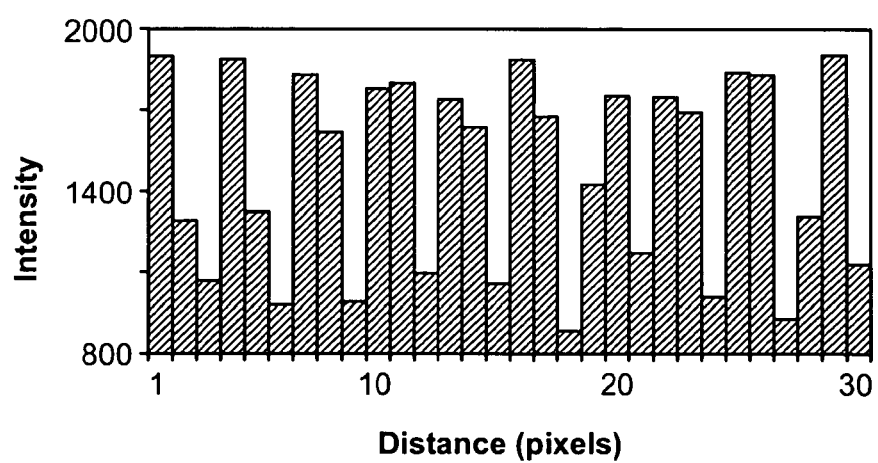

FIG. 4 shows the improvement of imaging efficiency and processing using 3×3 pixels on the CCD sensor to image each feature with our current bead arrays and microscope configuration. In this image, the fluorescence from each bead is projected onto a maximum of 2×2 pixels and each signal cluster is separated from one another by a single row and column of pixels. At this level of efficiency, more than $10^5$ beads may be imaged in a single field of view with our 1-megapixel camera. Profile plots across any 3 rows or columns in this figure reveal a clear distinction between the beads despite single pixel separation between adjacent beads. The upper panel shows a small region of a fluorescent image of an array of 1-μm superparamagnetic beads conjugated to Cy5-labeled DNA probes. A 10× objective was used and an EMCCD with 8×8 m² pixels was properly aligned to the array so that each feature may be imaged with 3×3 pixels. The lower panel shows the intensity profile of the pixels in the region highlighted by the rectangle. The periodicity of the signal clearly illustrates the separation between neighboring features. The different pixel intensities reflect the slight variation in the projection of the beads relative to the pixels on the CCD sensor. The scale bar is 4.8 μm.

Further improvements to both the imaging and packing efficiencies may be achieved by using smaller beads on an array with a reduced pitch as long as the format of the array matches that of the CCD sensor. For example, 4 pixels per feature may be achieved if a 10× objective and a CCD camera with 8×8 μm² pixels are used to image 0.8 μm or smaller beads assembled into 0.8 μm wells that have a center-to-center spacing of 1.6 μm. In this case each bead would fill only one pixel and be separated from each neighboring bead by a single pixel. If a CCD camera with a larger pixel size is used, e.g. 16×16 μm², the maximum imaging efficiency of 1 pixel per feature may be feasible. However, special features may need to be built into the array to serve as markers for precise alignment of the array to the pixels of the CCD sensor. The maximum packing efficiency that may be achieved depends upon the optics and the wavelength of light being used for imaging. For instance, when using a diffraction-limited objective with a high numerical aperture, e.g. a 40× oil lens with 1.3 NA, and visible light with a wavelength of 500 nm, the theoretical minimum spacing of the features is approximately 230 nm. The efficient production of wafer-scale arrays with features on this scale will require deep UV photolithography or nanoimprint lithography. The disclosed methods may be modified slightly to accommodate these fabrication methods by derivatizing the glass surface after the fabrication of the wells to prevent the destruction of the biotin moieties during the imprinting or etching steps (see, Hoff, J. D.; Cheng, L. J.; Meyhofer, E.; Guo, L. J.; Hunt, A. J. *Nano Lett.* 2004, 4, 853-857; Gao, H.; Tan, H.; Zhang, W.; Morton, K.; Chou, S. Y. *Nano Lett* 2006, 6, 2438-2441; Truskett, V. N.; Watts, M. P. *Trends Biotechnol.* 2006, 24, 312-317).

With the densities disclosed herein, more than 20 million beads may be arrayed in 1 cm². Also demonstrated is the ability to fabricate arrays of wells with dimensions as small as 0.8 μm and densities approaching 40 million wells per cm² over a large area on a cover glass with the stepper system we used. With the appropriate beads and arrays of wells, many copies of a human genome may be fragmented (e.g. 100-1000 bp), cloned and assembled onto a single glass cover slip. The genomic DNA clones may be generated by amplification of single DNA molecule on beads by PCR in microemulsions (see, Dressman, D.; Yan, H.; Traverso, G.; Kinzler, K. W.; Vogelstein, B. *Proc. Natl. Acad. Sci. U.S.A.* 2003, 100, 8817-8822). The usage of these high density arrays of DNA-conjugated microbeads may significantly increase the throughput and capacity of the emerging genome sequencing technologies and other array-based genomic and proteomic assays. In the disclosed methods, there is a minimal amount of space between each bead and overlap is virtually eliminated. These characteristics will also help reduce reagent waste and the need for expensive computer clusters to perform the image analysis and base calling algorithms.

Also disclosed are scalable methods for fabricating large-scale, high density arrays of DNA-conjugated superparamagnetic microbeads on glass cover slips. The single-step photolithographic process along with the speed and simplicity of the bead assembly step gives our approach many advantages over existing bead array technologies. The disclosed arrays typically have densities approaching 20 million beads per cm² may be produced over an area as large as 12 cm² using well established, production-scale manufacturing processes. The disclosed low-defect arrays are free of background caused by non-specifically bound beads and are compatible with automated processes, microfluidics devices and conventional microscopy. The disclosed highly ordered arrays, when properly sized and aligned to a given CCD sensor, may also greatly improve imaging efficiency and reduce the complexities of image processing. As few as 3×3 pixels are required to image each feature. By combining these arrays with the emerging sequencing technologies, the time and cost required to sequence a human genome may be reduced by at least one order of magnitude. The described method may also be used for fabricating and assembling arrays of other molecules such as antigens, lipids and proteins.

The disclosure also provides methods and automated systems for fabricating high density arrays of microwells for DNA amplification and sequencing applications. The disclosed methods and devices are based on recently developed techniques for creating perfectly ordered arrays of superparamagnetic microspheres (microbeads) on chemically derivatized glass slides. The disclosed methods utilizes a magnetic field to drastically enhance the assembly of the beads into the microwells. The wells may be fabricated in photoresist, for example positive-tone photoresist, using projection lithography and appropriately sized such that each well may accommodate only one bead. The beads may be held within the wells via biotin-avidin and/or biotin-streptavidin affinity binding. Once the assembly process is complete, DNA amplification or sequencing may be carried out on the DNA-conjugated beads. The high density arrays, which contain at least 25 million wells per square centimeter, have the potential to significantly enhance the throughput of currently available next-generation DNA sequencing methods and reduce the costs of sample preparations. Thus, the disclosure provides industry compatible arrays and systems that allow for the automated assembly of DNA-conjugated microspheres on the arrays.

The disclosure also provides methods and devices for preparing large arrays of microwells as a more efficient alternative for amplifying DNA on microspheres. In addition, the disclosed methods and devices may also allow the rapid assemble of high density ordered arrays of microspheres that provide as high as ten-fold greater throughput for a given sequencing device. The disclosed arrays may also be used in these newly emerging DNA sequencing devices.

The disclosure also provides devices which use large arrays of micron-sized reaction chambers contained within a microfluidics system, and is also capable of amplifying single DNA templates on microspheres. The disclosed microreactor arrays may use smaller volumes than conventional reactors; and is fully scalable; and is capable of precisely controlling the amount of product generated on each bead. The disclosed approach may also be more readily automated and may be capable of handling the task of amplifying the largest of genomes at a much higher throughput and lower cost than any other available method. Furthermore, the disclosed DNA amplification device may function in such a way that it may be used upstream with many of the newly emerging DNA sequencing technologies.

Figure 5:
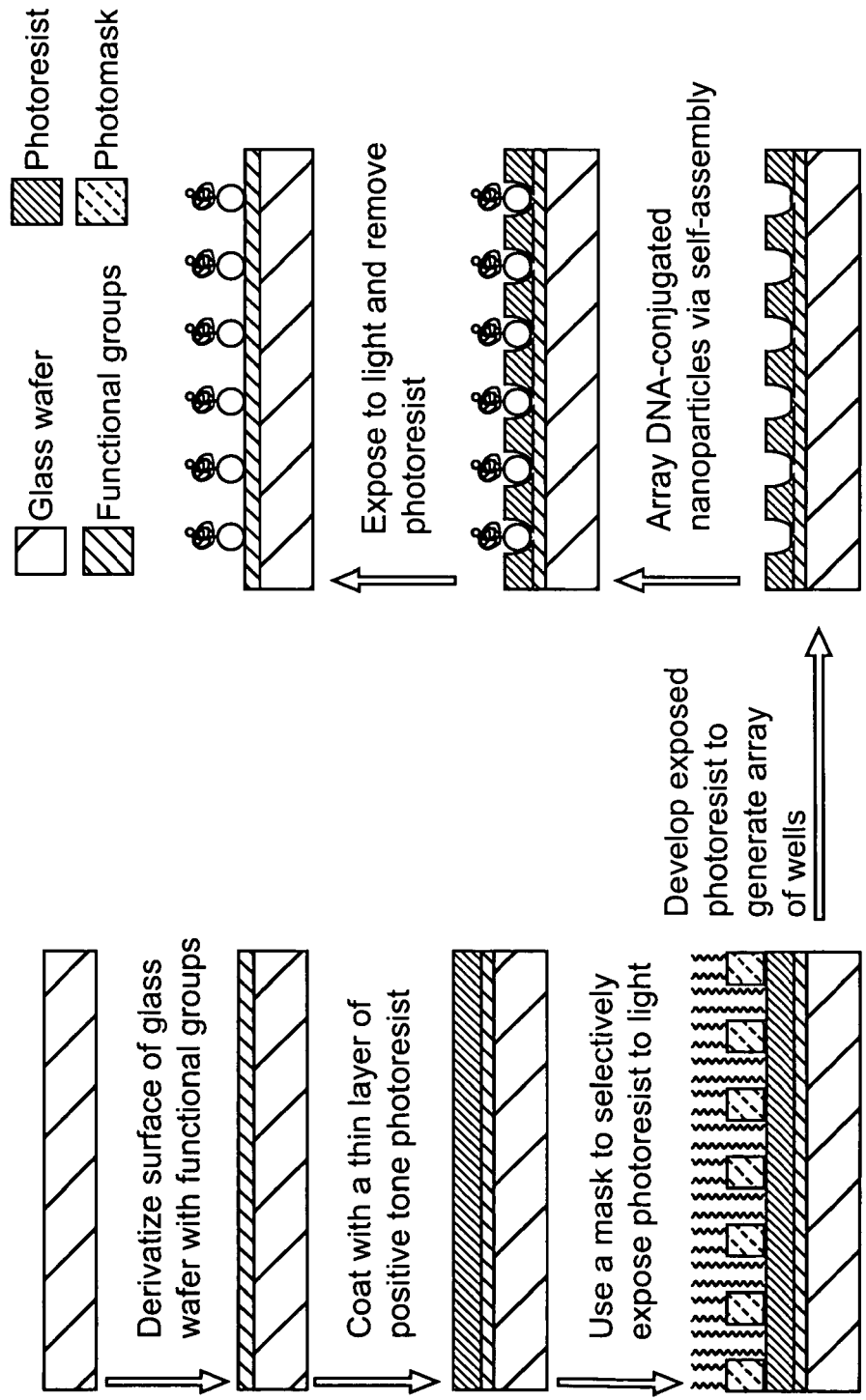
FIG. 5 illustrates an overview of the disclosed methods for fabricating high density biomolecular nanoarrays.

FIG. 5 illustrates an overview of the disclosed methods for fabricating high density biomolecular arrays using nanoparticles conjugated to biomolecules. The strategy for fabricating these highly ordered arrays involves using photolithographic techniques to provide an array of microwells. First, a glass surface is derivatized with functional groups. The glass is then spin-coated with a very thin layer of positive tone photoresist. The high density arrays of wells with sub-micron dimensions are fabricated in the photoresist using conventional photolithographic techniques. Nanoparticles conjugated to proteins or single DNA clones are then allowed to self-assemble into these wells, with only one nanoparticle occupying each well due to size constraints.

Alternatively, the disclosed methods use nanoparticles conjugated to a biomolecule which may be actively drawn towards the surface of the array via an electric field. In this approach, a thin layer of polyacrylamide solution is spin-coated onto a conducting surface and then cross-linked via a photoactivated cross-linker. Also within this polyacrylamide solution are small amounts of biotin-derivatized and/or amine-derivatized acrylamide polymers to aid in the surface binding and affinity capture in subsequent steps. A layer of photoresist is spin-coated on top of the polyacrylamide layer and high density arrays of wells with sub-micron dimensions are then fabricated in the photoresist using conventional photolithographic techniques.

In both of these approaches, the nanoparticles become fixed within the wells via biotin-avidin and/or biotin-streptavidin binding, which may only occur at the bottom of the wells where the surface of the derivatized slide or polyacrylimide is exposed. Non-specifically bound nanoparticles may be easily removed by removing the remaining photoresist, thereby leaving us with virtually no background. This digital characteristic is critical for high-throughput DNA sequencing and other applications, and we have capitalized on the digital nature of photolithographic processes to give our arrays this property.

The current art does not allow for the quick and clean construction of wafer-scale high density arrays of single DNA clones. The disclosed arrays are perfectly ordered and each spot on the array contains a unique DNA clone. The disclosed methods are conducive to rapid manufacturing using conventional photolithographic techniques.

The disclosed methods provide the ability to generate high density arrays of sub-micron wells in photoresist. The size of these wells may be controlled by varying the exposure and chemical etching parameters. The methods also provide the ability to generate high density arrays of nanoparticles by filling these wells via a self-assembly process, wherein the nanoparticles remain attached and ordered even after the photoresist has been removed chemically.

With reference to FIG. 5, a procedure for fabricating high density arrays of nanoparticles conjugated to DNA is as follows: (1) Glass slides are cleaned and derivatized with amine groups. Biotin moieties are then covalently attached to these amine groups via a long linker arm through an amide bond. (2) The glass slides are coated with a 500 nm layer of positive tone photoresist (sold under the trademark MICROPOSIT™ S1805™). (3) The photoresist is selectively exposed to ultraviolet light through a chrome mask with a projection lithography stepper system (GCA Autostep 200). (4) Wafer-scale, high density arrays of micrometer-sized wells are generated upon the development of the exposed photoresist. (5) The array is enclosed within a micro fluidics device and a suspension of nanoparticles conjugated to a biomolecule, i.e., protein or DNA, is introduced into the chamber. The size of the wells are controlled such that only one nanoparticle may fit into each well in the array. Upon entering the wells, the nanoparticles are anchored down via biotin-avidin and/or biotin-streptavidin binding. Excess nanoparticles are washed away whereas the non-specifically bound nanoparticles may still remain on the surface of the photoresist. (6) These nanoparticles are removed by a brief treatment with a saturated solution of biotin followed by a photoresist lift-off process using ethanol. The result is a high density array of single microspheres with virtually no background.

Figure 6:
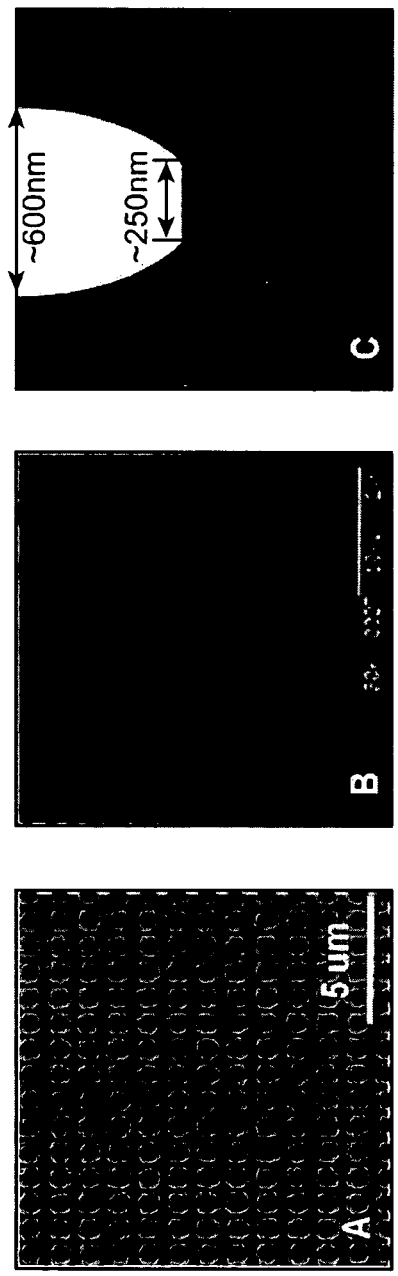
FIG. 6 illustrates (A) the light micrograph of a small part of an array of wells at a density of 100 million wells per square centimeter; (B) the scanning electron microscope (SEM) image of a cross-sectional view of an array of wells; and (C) a well with parabolic geometry and dimensions estimated from SEM images.

FIG. 6 illustrates a light micrograph of a small part of an array of wells at a density of 100 million wells per square centimeter (see (A)). Also in FIG. 6 is the SEM image of a cross-sectional view of an array of wells (see (B)). Finally, a well with parabolic geometry and dimensions estimated from SEM images is provided (see (C)).

Figure 7:
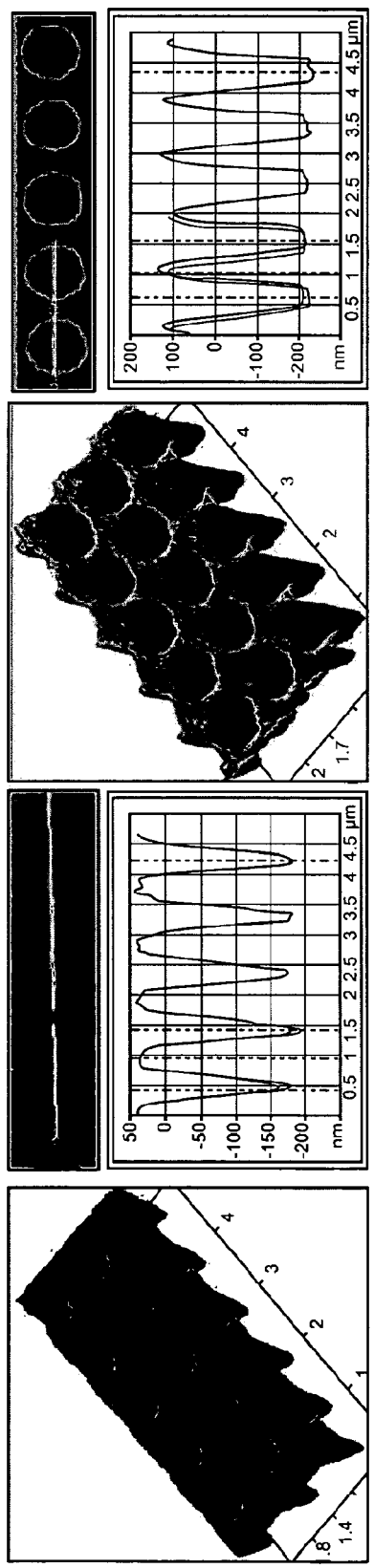
FIG. 7 illustrates the atomic force microscopy (AFM) images of an array of wells produced with different photolithographic exposure dosages.

FIG. 7 illustrates the AFM images of an array of wells produced with different photolithographic exposure dosages. The disclosure provides methods for controlling the dimensions of the wells by adjusting the exposure dosage of the photoresist. This property provides an additional degree of freedom when attempting to match microspheres of a given size to an arrays of wells. This ensures that each well may accommodate only a single bead. In FIG. 7, the AFM images of an array of wells produced with different exposure dosages shows that the center-to-center spacing of the wells remains the same but the dimensions of the wells may be controlled by varying the exposure dosages used during photolithographic processing. Also shown are isometric and top views of two arrays of wells generated with two different exposure times. The array on the left was produced using a shorter exposure time than the one on the right.

Figure 8:
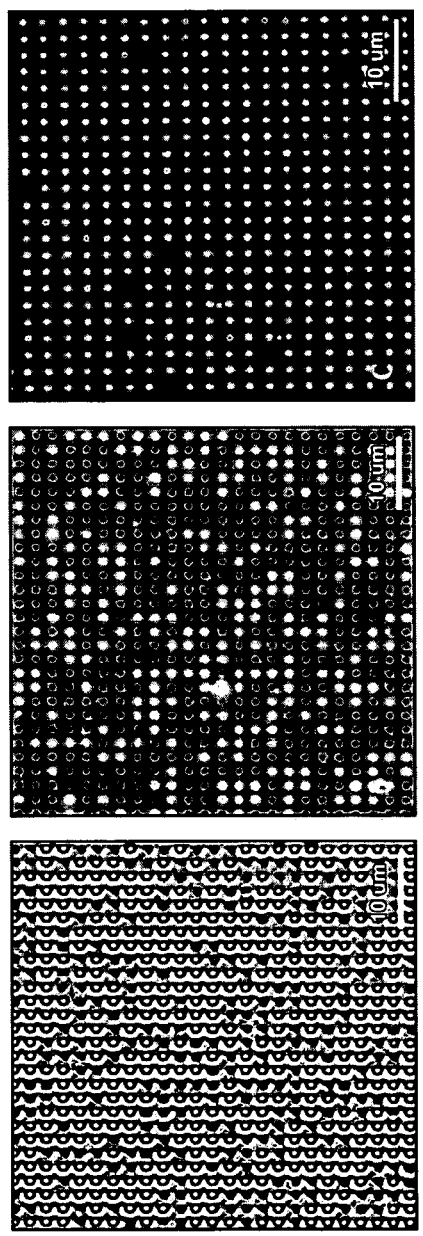
FIG. 8 illustrates the light micrograph of an array of 1 µm wells that are in the process of being filled with functionalized nanoparticles (820 nm) via self-assembly (see (A)); the fluorescence micrograph of the same array shown in (A) (see (B)); and an fluorescence micrograph of an array of fluorescent nanoparticles after the removal of the photoresist (see (C)).

FIG. 8 illustrates the light micrograph of an array of 1 μm wells that are in the process of being filled with functionalized nanoparticles (820 nm) via self-assembly (see (A)); the fluorescence micrograph of the same array shown in (A) (see (B)); and an fluorescence micrograph of an array of fluorescent nanoparticles after the removal of the photoresist (see (C)). The disclosure provides methods for fine tuning the dimensions of wells by adjusting the exposure dosage of the photoresist. This property provides an additional degree of freedom when attempting to match microspheres of a given size to an arrays of wells. This ensures that each well may accommodate only a single bead. Once the beads have assembled into the wells of the arrays, they may be fixed via biotin-avidin and/or biotin-streptavidin binding. Removal of the photoresist may then be achieved without affecting the ordered arrangement of these entities. The perfectly order arrays of beads include: (A) a light micrograph of an array of 1.2-micron wells that have been filled with 1-micron superparamagnetic microspheres via the application of an external magnetic field. biotin-avidin and/or biotin-streptavidin affinity binding is responsible for holding the beads in the wells. This particular array was fabricated on a 170-micron-thick glass cover slip and contained a total of 300 million wells; (B) shows a light micrograph of the same array shown in (A) after the removal of the photoresist; and (C) shows an AFM image of an array of 1.05-micron-diameter superparamagnetic microspheres (MyOne Dynabeads) in an ordered array on a glass slide after the removal of the photoresist.

Figure 9:
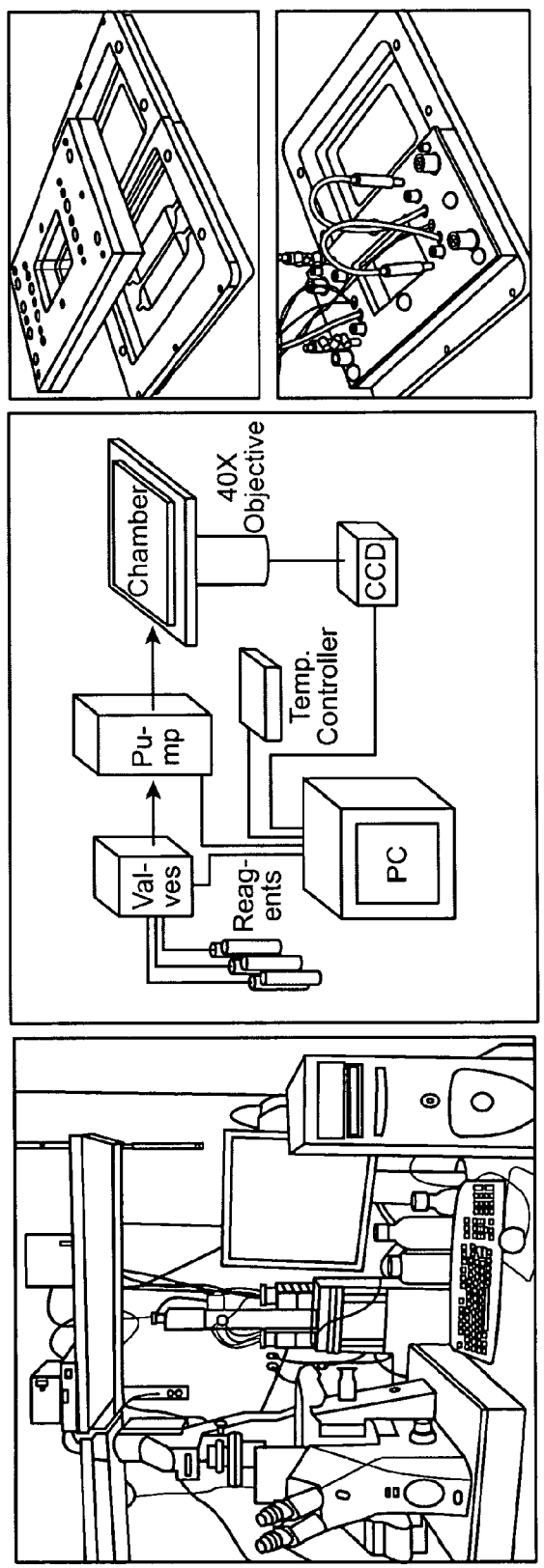
FIG. 9 illustrates a device for performing the magnetic manipulation of beads using a syringe pump, a multi-port valve, a microfluidic flowcell with temperature control, a microscope, and a computer that controls all the components.

FIG. 9 illustrates a device for performing the magnetic manipulation of beads using a syringe pump, a multi-port valve, a microfluidic flowcell with temperature control, a microscope, and a computer that controls all the components. In particular, FIG. 9 provides a schematic for an automated system for fabricating high density arrays of microwells for DNA amplification and sequencing applications, wherein (A) shows the current fluidics and imaging setup for assembling beads on arrays and amplifying DNA on the beads; (B) shows a schematic of the components involved in the bead assembly and DNA amplification processes; (C) shows a schematic of one of the chambers that contains the array; and (D) shows a prototype of the chamber design shown in (C). In this device, the glass slide or cover slip containing the array of wells is first loaded into the flowcell. The pump and valve deliver various reagents and the bead solution to the device. The application of the magnetic field is conducted manually using a permanent bar magnet. The microscope allows for real time monitoring of the well-filling process. Excess beads may be recycled or discarded and several automated washing steps are carried out to remove any remaining unbound beads. An ethanol solution may then be introduced into the chamber to dissolve away the photoresist and any non-specifically bound beads. If the device is to be used to amplify DNA on the beads then the photoresist may be left in place and the reaction solution may be delivered to the chamber after removing all unbound beads.

The disclosed methods and devices allow for commercially viable product lines of industry compatible arrays of wells that may be used to capture, in an ordered and high density format, DNA-conjugated microspheres. The basic device may be a disposable flowcell with a microfabricated array of wells on a glass substrate. The glass substrate may be permanently bonded to an injection-molded plastic or glass top plate. The flowcell may have microfluidic channels and tubing connections for coupling the device to a pump and valve assembly. Customers may be able to select an array with wells that are sized to their particular application and microspheres being used. In addition, the overall size and design of the devices may also be compatible with their downstream sequencing equipment. Other design criteria include reliability, disposability, and compatibility with mass manufacturing methods.

The devices and processes disclosed are based on the recently developed proprietary technique as described above for creating perfectly-ordered arrays of superparamagnetic microspheres (microbeads) on chemically derivatized glass slides. The arrays are fabricated on glass slides or cover slips derivatized with functional groups. The slides are spin-coated with a very thin layer of positive tone photoresist. Micrometer-sized wells are then fabricated in the photoresist using projection lithography. A stepper system provides the ability to print large arrays in a highly reproducible manner. Superparamagnetic microspheres conjugated to single DNA clones are then driven into the wells via an external magnetic field, with only one bead occupying each well because of size constraints. The beads are fixed within the wells via biotin-avidin and/or biotin-streptavidin binding or covalent bonds, which may only occur at the bottom of the wells where the surface of the slide is exposed. Non-specifically bound beads may be easily removed by removing the remaining photoresist with a brief exposure to ethanol, thereby leaving us with virtually no background.

The disclosed flowcell may be compatible with the DNA sequencing devices being currently being developed, and the commercially available Solexa 1G Genetic Analyzer. The disclosed arrays may be used to rapidly assemble high density ordered arrays of microspheres that may provide as high as ten-fold greater throughput for the sequencing devices. The arrays may be used in union with these newly emerging DNA sequencing devices. In addition, the use of the large arrays of microwells are a more efficient alternative for amplifying DNA on microspheres. The disclosure also includes a flowcell with built-in microfluidics and precise temperature control for performing this process as shown in FIG. 9.

Also disclosed herein, is an integrated, self-contained system to automate the assembly of superparamagnetic microspheres on the arrays in the disclosed devices. The end users may use these devices to produce a highly ordered array of DNA clones to be used in their preferred sequencing methods. This system may also be capable of supporting the amplification of DNA on magnetic beads by using the wells as microwells in which DNA synthesis will take place. The system may include reagent reservoirs, a pump and valves, a heating block, a magnetic field source, and an imaging system to monitor the well filling and amplification processes.

The disclosed devices may be inserted into the system along with the reagents and beads. The pumps and valves may automatically deliver the appropriate reagents to the device using a simple software package that may be run on any PC. A pulsed magnetic field may be generated from electromagnets to accelerate the filling of the wells with beads. These magnets may also be used to help remove non-specifically bound beads by reversing the direction of the gradient and thus driving excess beads from the surface of the array. The imaging system may also allow for real time monitoring of this process from the same computer that is used to run the control software. The system may be constructed with inexpensive optical components. Alternatively, any microscope system with a digital camera may be used.

The bead filling process is the same as above when the device is used for amplification. For this process, however, the chamber is filled with a reaction solution containing enzymes, nucleotides, and primers. The contents of this solution are allowed to diffuse into the wells and then excess solution is removed from the chamber, leaving behind solution in the wells only. The chamber temperature is then increased to a suitable temperature for DNA synthesis to occur via one of two unique processes known as linear or hyperbranched rolling circle amplification. Once the amplification step is complete, a solution is introduced into the chamber to cleave a reducible bond in the biotin linker holding the beads in the microwells. A magnetic field may be used to draw the beads out of their wells and into the bulk solution. The solution is removed and downstream processing steps may be performed to isolate those beads that contain the amplified product. These beads may then be placed on an array for DNA sequencing. Alternatively, the amplified beads may be left in place and sequenced on the same array in the user's preferred DNA sequencing equipment The commercialization of faster and cheaper DNA sequencing devices will soon prove to be an extremely lucrative venture. Many biotechnology companies have devoted considerable resources towards the development of novel DNA sequencing technologies. Examples include 454 Life Sciences, Solexa/Illumina, Applied Biosystems, and Pacific Biosciences.

In the 454 technology, single DNA molecular clones generated by emPCR are distributed onto arrays of wells etched into the faceplates of optical fiber bundles. The DNA sequences are decoded by a process called pyrosequencing. 454 Life Sciences began marketing a new sequencing platform in October 2005 but their technology is only marginally cheaper than what is currently available because a limited number of templates (a few million) may be sequenced with one device.

Other areas in which this technology may prove to be very useful include protein array technology and biosensors. Current protein array fabrication methods require spotting of individual proteins onto chips using slow and cumbersome spotters. Furthermore, the densities of these arrays are quite low due to the relatively large droplets dispensed by these devices. The disclosed methods may eliminate the need for a spotter and allow one to easily fabricate extremely high density protein arrays by coupling the proteins to micro- or nanospheres and then allowing them to self-assemble in the wells of our arrays.

The disclosed methods may be useful in the field of genome sequencing. For DNA sequencing applications, single DNA molecules or amplified clones attached to nanoparticles may be fixed within the wells of the array via self-assembly and an affinity capture mechanism. This method will provide the means for separating and ordering single DNA molecules or clones representing more than 100 copies of a human genome onto a small chip. Unprecedented sample throughput and cost reductions in genome sequencing may be achieved with these perfectly-ordered high density nanoarrays of DNA templates. Sequencing platforms currently being developed by many companies use microbeads with DNA molecular clones randomly distributed onto a surface, which result in low imaging efficiency and throughput. The application of our biomolecular nanoarray technology may tremendously improve the throughputs of these sequencing technologies.

Other areas in which this technology may prove to be very useful include protein array technology and biosensors. Current protein array fabrication methods require spotting of individual proteins onto chips using slow and cumbersome spotters. Furthermore, the densities of these arrays are quite low due to the relatively large droplets dispensed by these devices. The disclosed methods eliminate the need for a spotter and allow one to easily fabricate extremely high density protein arrays by coupling the proteins to nanoparticles and then allowing them to self-assemble in the wells of the arrays.

Examples

Chemical Derivatization of Glass Surfaces

50×75×0.170 $mm^3$ borosilicate glass cover slips (Erie Scientific, Portsmouth, N.H.) were washed with a detergent solution and rinsed with 18 M-Ohm/cm de-ionized water. They were further cleaned by soaking in methanol and then acetone for 5 minutes each in an ultrasonic bath and dried in a convection oven at 110° C. for 10 minutes. The cover slips were then soaked in a 2 M nitric acid solution for 30 minutes at room temperature and rinsed with de-ionized water. Silanization was performed using a 2% solution of 3-aminopropyl-triethoxy-silane (Gelest Inc., Morrisville, Pa.) in 95:5 acetone: water for 15 minutes at room temperature. The cover slips were then rinsed 3 times with acetone and cured at 110° C. for 15 minutes in a convection oven. A 1 mM solution of N-hydroxylsuccinimidyl-PEG-biotin, MW 5000 (Nektar Therapeutics, San Carlos, Calif.) in dry N,N-dimethylformamide with 1 mM triethylamine was prepared and 300 uL was spotted onto each cover slip and then covered with another cover slip using a #1 cover slip as a spacer. After one hour of incubation at room temperature, the cover slips were rinsed with acetone and treated with a 1% ammonium hydroxide+ 0.1% sodium dodecyl sulfate solution for 15 minutes. The cover slips were rinsed with de-ionized water followed by acetone and dried at 65° C. for 10 minutes. The derivatized cover slips were stored in a vacuum desiccator.

Microfabrication

A layer of photoresist (sold under the trademark MICROPOSIT™ S1805™; Rohm & Haas) about 500 nm thick was applied to the surface efthe of the glass by spinning at 3500 rpm for 30 seconds with a spin coater. The glass was then heated on a hotplate at 110° C. for 60 seconds. The array of wells were patterned by a 0.2 second exposure to 365 nm light (~475 $mW/cm^2$) through a chrome-on-quartz photomask using a wafer stepper system (GCA Autostep™ 200) equipped with an Olympus® 2145 lens (5× reduction/0.45 NA). The photoresist was developed in MIF 701 (Rohm & Haas) for 60 seconds at room temperature and then rinsed with water and dried with nitrogen gas.

Conjugation of DNA to Microbeads

Three oligonucleotides with both biotin and fluorescence dye labels are: 5'Fluorescein-TCCAGTTGACCT-GAGAGTC-TEG-biotin-3' (SEQ ID NO:1), 5'-Cy3-TCCT-GACTGAGTAGCATCG-TEG-biotin-3' (SEQ ID NO:2) and 5'-CySTCACGTACTGAGGTCGTCA-TEG-biotin-3' (SEQ ID NO:3). The microbeads were prepared by adding drop wise a 10 μM solution of a labeled oligonucleotide to 0.1% (w/v) suspension of 1-μm streptavidin-coated superparamagnetic beads (Dynal MyOne™, Invitrogen Corporation, Carlsbad, Calif.) in a DNA binding buffer (10 mM Tris-HCl, pH 7.5, 2.0 M NaCl, 1 mM EDTA). The amount of the biotinylated oligonucleotides is sufficient to bind approximately one third of the biotin binding sites on the beads (~150,000 oligonucleotides per bead). The mixture was shaken for 2 hours at room temperature and washed 3 times with a wash buffer (WB: 50 mM sodium phosphate, pH 7.05, 150 mM NaCl, 1 mM EDTA, 0.02% Tween-20). The beads were re-suspended in the wash buffer to give a final concentration of 0.25% (w/v). For the image (FIG. 3), the mixture contained the 3 bead populations in roughly equal molar ratio. For the gray-scale image (FIG. 4), the beads contained only the Cy5-labeled oligonucleotides.

Rapid Magnetic Assembly of Microbead Arrays

The microbead assembly was performed within a flow cell, which consists of a 1 mm thick glass slide, a 250 μm-thick silicone rubber gasket and the cover glass with the array (FIG. 1). Prior to the assembly of the flow cell, small holes were drilled through the slide and tubing connectors were fixed to the slide with epoxy. The gasket was laid onto the slide and the middle portion was cut out to form the flow chamber. The cover glass was aligned and pressed to the gasket to form a liquid-tight seal between the slide and the cover glass.

The chamber was first rinsed with a wash buffer (WB) and then the suspension containing the DNA-conjugated microbeads was introduced into the chamber via a syringe pump. A small neodymium iron boron magnet (5848K21, McMaster-Carr) was quickly dragged along the back side of the array to pull the beads into the wells. The suspension was slightly agitated using the syringe pump and then the beads were drawn back towards the surface of the array using the magnet. This process was repeated 3-5 times. The suspension containing any excess beads was then reclaimed and the chamber was washed extensively with the wash buffer. The photoresist was dissolved by briefly exposing it to a 95% ethanol solution. The ethanol was then removed by rinsing with the wash buffer. For more sensitive biomolecules, the photoresist may also be removed under milder conditions using a flood exposure followed by a brief wash with a basic buffer solution.

Bright Field and Fluorescence Microscopy

Bright field images were acquired with a 63×/0.7 NA objective on a DM LFSA microscope (Leica Microsystems) equipped with an ORCA-ER CCD camera (Hamamatsu Photonics). Fluorescent images were acquired with an Axiovert 200M epifluorescence microscope (Carl Zeiss). The chamber containing the bead array was placed on a BioPrecision XY microscope stage (Ludl Electronic Products Ltd.) and illuminated with a Lambda DG-5 light source (Sutter Instrument Co.) using FITC, Cy3, and Cy5 excitation filters and a Pinkel set filter cube (Semrock). The images were acquired with either a 10×/0.45 NA or a 20×10.80 NA objective (Carl Zeiss) and an iXon Plus 1-megapixel EMCCD camera with 8×8 $μm^2$ pixels (Andor Technology). Background subtraction and image processing was performed with ImageJ (Abramoff, M. D., Magelhaes, P. J., Ram, S. J. *Biophotonics Intl.* 2004, 11, 36-42).

AFM Imaging

The atomic force micrograph was acquired with a Multi-mode Scanning Probe Microscope and NanoScope IV controller (Digital Instruments, Veeco Metrology Group). The instrument was operated in tapping mode using an AS-12NM scanner and a RTESP probe (Veeco Probes). Height and phase information was recorded using the NanoScope software and image processing and rendering was performed using WSxM (Horcas, I.; Fernandez, R.; Gomez-Rodriguez, J. M.; Colchero, J.; Gomez-Herrero, J.; Baro, A. M. *Rev. Sci. Instrum.* 2007, 78, 013705).

SEM Imaging

SEMs were acquired with a Phillips XL30 Environmental SEM in high vacuum mode at 10 kV. All samples were washed with deionized water, air dried, and then sputter coated with a thin layer of gold or chromium using a Denton Discovery 18 sputter system or EMITECH K575X sputter tool prior to SEM imaging.

While the principles of the disclosure have been described above in connection with specific apparatuses and methods, it is to be clearly understood that this description is made only by way of example and not as limitation on the scope of the disclosure.

What is claimed is:

1. A method for rapidly assembling a high density biomolecular array, the method comprising the steps of:
   a) patterning an array of wells into photoresist on a surface by photolithography;
   b) assembling a suspension of magnetic biomolecular particles into the array of wells;
   c) immobilizing the magnetic biomolecular particles to the surface via affinity binding; and
   d) removing the unbound suspension of magnetic biomolecular particles and photoresist from the surface to provide the high density biomolecular array.

2. The method of claim 1, wherein the suspension of magnetic biomolecular particles is a suspension of superparamagnetic microbeads conjugated to a biomolecule, wherein the superparamagnetic microbeads are assembled into the array of wells using a magnet.

3. The method of claim 1, wherein the surface is a glass surface.

4. The method of claim 3, wherein the glass surface is derivatized with silane and biotin, and/or avidin and/or streptavidin.

5. The method of claim 4, wherein the glass surface is spin-coated with photoresist.

6. The method of claim 5, wherein the photoresist is sold under the trademark MICROPOSIT™ S1805™.

7. The method of claim 6, wherein the array of wells are patterned by photolithography using a 0.2 second exposure to 365 nM light (~475 mW/cm$^2$) through a chrome-on-quartz photomask using a wafer stepper system sold under the trademark GCA™ Autostep™ 200) equipped with a lens sold under the trademark Olympus™ 2145 (5× reduction/0.45 NA).

8. The method of claim 7, wherein the size of the array of wells varies with the exposure and chemical etching parameters of the photolithography technique.

9. The method of claim 8, wherein the array of wells has a density of about 100 million wells per square centimeter.

10. The method of claim 9, wherein the array of wells has a parabolic geometry wherein the top of a well is about 600 nm in diameter and the bottom of a well is about 250 nm in diameter.

11. The method of claim 2, wherein the superparamagnetic microbeads are coated with biotin, and/or avidin and/or streptavidin.

12. The method of claim 11, wherein the superparamagnetic microbeads are suspended in a buffer.

13. The method of claim 12, wherein the assembly of the superparamagnetic microbeads into the array of wells occurs in a flow cell.

14. The method of claim 13, wherein the superparamagnetic microbeads are assembled into the array of wells using a neodymium iron boron magnet.

15. The method of claim 14, wherein each well contains a single superparamagnetic microbead.

16. The method of claim 15, wherein the superparamagnetic microbeads are immobilized in the array of wells via biotin-avidin and/or biotin-streptavidin affinity binding.

17. The method of claim 2, wherein the high density biomolecular array is a high density protein array, or a high density DNA array of biomolecules.

* * * * *

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: Residue 1 modified by fluorescein
<220> FEATURE:
<221> NAME/KEY: modified_base
<222> LOCATION: (19)..(19)
<223> OTHER INFORMATION: Residue 19 modified by TEG-biotin

<400> SEQUENCE: 1
tccagttgac ctgagagtc                                               19

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: Residue 1 modified by Cy3
<220> FEATURE:
<221> NAME/KEY: modified_base
<222> LOCATION: (19)..(19)
<223> OTHER INFORMATION: Residue 19 modified by TEG-biotin

<400> SEQUENCE: 2
tcctgactga gtagcatcg                                               19

<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: Residue 1 modified by Cy5
<220> FEATURE:
<221> NAME/KEY: modified_base
<222> LOCATION: (19)..(19)
<223> OTHER INFORMATION: Residue 19 modified by TEG-biotin

<400> SEQUENCE: 3
tcacgtactg aggtcgtca                                               19
```